United States Patent
Guillama et al.

(10) Patent No.: US 11,621,063 B2
(45) Date of Patent: *Apr. 4, 2023

(54) GRAPHICAL USER INTERFACE WITH INTELLIGENT ICONS

(71) Applicant: The Quantum Group, Inc., Lake Worth, FL (US)

(72) Inventors: Noel J. Guillama, Wellington, FL (US); Chester A. Heath, Boca Raton, FL (US)

(73) Assignees: The Quantum Group, Inc., Greenacres, FL (US); Noel J. Guillama, Wellington, FL (US)

( * ) Notice: Subject to any disclaimer, the term of this patent is extended or adjusted under 35 U.S.C. 154(b) by 246 days.

This patent is subject to a terminal disclaimer.

(21) Appl. No.: 17/106,061

(22) Filed: Nov. 27, 2020

(65) Prior Publication Data

US 2021/0151143 A1 May 20, 2021

Related U.S. Application Data

(63) Continuation of application No. 15/042,231, filed on Feb. 12, 2016, now Pat. No. 10,878,946.

(60) Provisional application No. 62/115,344, filed on Feb. 12, 2015.

(51) Int. Cl.
*G16H 10/60* (2018.01)
*G16Z 99/00* (2019.01)

(52) U.S. Cl.
CPC ............. *G16H 10/60* (2018.01); *G16Z 99/00* (2019.02)

(58) Field of Classification Search
CPC ....................................................... G16H 80/00
See application file for complete search history.

(56) References Cited

U.S. PATENT DOCUMENTS

| | | | |
|---|---|---|---|
| 2003/0110384 A1* | 6/2003 | Carro | H04L 9/3242 713/181 |
| 2005/0286736 A1 | 12/2005 | Rhoads | |
| 2008/0103836 A1* | 5/2008 | Park | G06Q 40/08 705/2 |

(Continued)

OTHER PUBLICATIONS

Maiti, C. et al., "Data Hiding in Images Using Some Efficient Steganograpy Techniques," Asansol Engineering College, pp. 195-203 (2011).

*Primary Examiner* — John A Pauls
(74) *Attorney, Agent, or Firm* — Nixon Peabody LLP

(57) ABSTRACT

A system for signaling coordinated workers in a common goal through intelligent icons transferred across networks to computer screens. The system can comprise one or more electronic data processors. The system can also include a module configured to execute on the more or more electronic data processors, where the module can be configured to display a plurality of intelligent icons, each containing authorizing information that is retained in a file associated with a authorizing entity on a computer screen. The intelligent icons can be potentially loaned to authorized individuals on a list and used to authenticate users of the system with biometric, image, machine readable codes stored surreptitiously within the intelligent icon. Also, the intelligent icon can be used for friend-foe identification in battlefield and homeland security/border control scenarios.

18 Claims, 10 Drawing Sheets

(56) References Cited

U.S. PATENT DOCUMENTS

2010/0125175 A1\* 5/2010 Vallone ................ A61B 5/7435
              600/300
2011/0311026 A1 12/2011 Lalena
2014/0018708 A1 1/2014 Dunbar \* cited by examiner

1000

1050

GRAPHICAL USER INTERFACE WITH INTELLIGENT ICONS

CROSS-REFERENCE TO RELATED APPLICATIONS

This application is a continuation of U.S. application Ser. No. 15/042,231, filed Feb. 12, 2016, which claims priority to and the benefit of U.S. Provisional Patent Application No. 62/115,344, filed Feb. 12, 2015, each of which is hereby incorporated by reference in its entirety.

FIELD OF THE INVENTION

The present invention is related to Graphic User Interfaces (GUIs) and more particularly, to GUIs employing intelligent icons.

BACKGROUND OF THE INVENTION

The Affordable Care Act has resulted in millions of previously uninsured patients being added to the United States healthcare system. Many of these new patients will have chronic maladies requiring treatment and diagnosis, potentially by teams of health care providers. This wave of new patients will put particular pressure on providers' limited resources, while still requiring an increase in medical provider productivity and improved diagnostic accuracy. Stated differently, improvements in provider efficiency will be required to meet the increasing demands and requirements under the Affordance Care Act. To this end, it will become more important for providers to have as much information as possible about their patients, especially existing diagnosis and treatment information associated with other providers. In particular, share it is especially imperative to provide concise alerts to coordinating healthcare providers when maladies are discovered, and to broadcast these alerts rapidly amongst the teams. Further alerts should lead efficiently to patient centric diagnostic and treatment records. These alerts should easily lend toward peer consult, specialist cooperation and support the freedom for specialists to react independently in emergency and trauma situations. Lastly, these alerts should provide foundation for research and data mining to spot patterns where knowledge can be applied generally to all patients suffering similar maladies.

However, one issue with the sharing of information discussed above are the limitations imposed on providers by the Health Insurance Portability and Accountability Act. In particular, limitation regarding security and privacy requirements for patient records. Thus, simply sharing the information, via notifications or the like, is insufficient. Rather, such sharing must be performed with patient authorization and under secure conditions. Accordingly, there is a need to provide systems and methods for providing notifications to different providers about patients in a safe and secure manner.

SUMMARY OF THE INVENTION

The present invention is related to Graphic User Interfaces (GUIs) and more particularly, to GUIs employing intelligent icons. In a first embodiment, there is provided a computer-implemented method. The method includes receiving one or more intelligent icons from one or more client devices, aggregating a portion of the one or more intelligent icons associated with a same identifier to define a record for the identifier, and transmitting the record to at least one of the client devices. In the method, each of the intelligent icons comprises a image comprising the base image modified to encode data associated with the identifier, where the encoded data is defined by a plurality of single bit changes in the base image.

In the first embodiment, the plurality of single bit changes can be associated with the least significant bits representing the base image. Further, the base image for each of the one or more intelligent icons can correspond to at least a portion of the encoded data.

In the first embodiment, the encoded data can include at least one data item. The at least one data item can include at least one of an image, a machine readable code, unencrypted alpha-numeric content, encrypted alphanumeric content, a link, or an executable program. In some cases, each of the at least one data item is encoded into bits of different bit positions of the base image, such as different bit positions of the base image corresponding to the least significant bits.

In a second embodiment, there is provided a computer-implemented method. The method can include collecting data associated with an identifier, obtaining a base image, and generating a modified version of the base image to yield an intelligent icon, wherein the modified version of the base image is generated by introducing a plurality of single bit changes into the base image that represent the encoded data.

In the second embodiment, the plurality of single bit changes can be associated with the least significant bits representing the base image.

In the second embodiment, the obtaining can include selecting the base image to correspond to at least a portion of the encoded data. Further the selecting can include analyzing the data to extract one or more characteristics associated with the data and electing the base image from a pool of base images based on the characteristics.

In the second embodiment, the encoded data can include at least one data item. The at least one data item can include at least one of an image, a machine readable code, unencrypted alpha-numeric content, encrypted alphanumeric content, a link, or an executable program. In some cases, each of the at least one data item is encoded into bits of different bit positions of the base image, such as different bit positions of the base image corresponding to the least significant bits.

In the second embodiment, the method can include receiving a record associated with the identifier, wherein the record includes at least one of the intelligent icon or another intelligent icon associated with the identifier, the other intelligent icon being a modified version of another base image modified to encode other data associated with the identifier, where the other data is defined by a plurality of single bit changes in the another base image.

In other embodiments, there is provided a computer-readable medium having stored thereon a computer program, where the computer program includes plurality of instructions for causing a computer to perform the methods of either of the first or second embodiments.

In still other embodiments, there is provided a system comprising a processor and a computer-readable medium having stored thereon a plurality of instructions for causing a processor to perform the methods of either of the first or second embodiments.

In all embodiments, the intelligent icons can be configured to have various types of functionality. Further in all embodiments, there is the potential to include password protection, encryption and other means of access controls for privacy and security control to the functions of the intelligent icon.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

Figure 1:
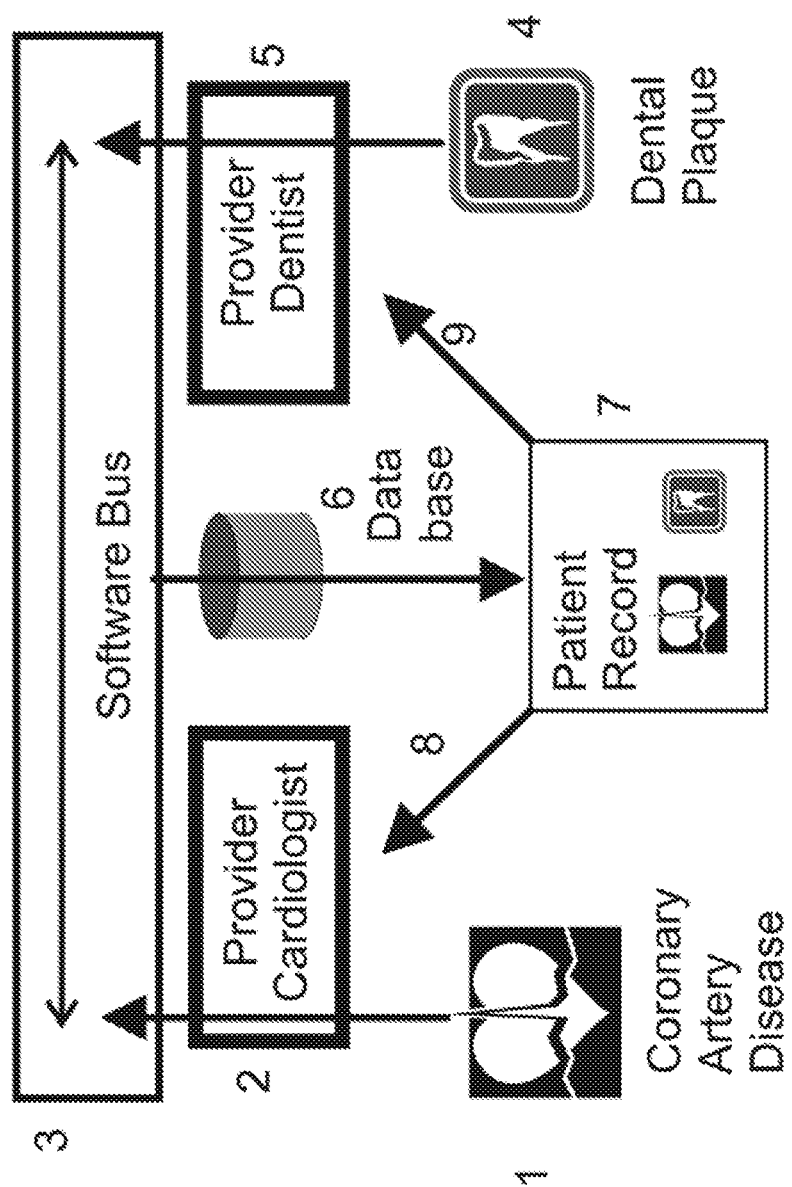
FIG. 1 is a system for presentation of patient records including intelligent icons in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Although the present invention will be described at time with reference to particular hardware and/or software components, this is solely for ease of illustration. In the various embodiments, other hardware and/or software components can be used without limitation, including but not limited to the components discussed below with respect to FIGS. 10A and 10B.

The present invention is directed to systems and methods for Graphic User Interfaces with intelligent icons on computer screens within a computer system. The invention enables the secure, but recoverable embedding of information in the displayed icon relating to the meaning of the intelligent icons linked information.

Some embodiments of the invention are directed to systems and methods for presenting alerts in the form of intelligent icons, or "Medikons," to coordinate medical services in healthcare systems. An exemplary system can comprise one or more electronic data processors, possibly interconnected by a network. Each system can also include a module configured to execute on the more or more electronic data processors, where the module can be configured to display a plurality of intelligent icons on a computer screen, each retained in a file associated with a particular individual in a common database system.

In some embodiments, multiple intelligent icons would be displayed where each icon can display a unique figure or image, typically indicating a specific medical condition. The multiple intelligent icons can be prominently displayed on the patient's medical record. In the various embodiments, the multiple intelligent icons can be associated with a single individual or group of individuals, depending on the information being retrieved by the provider.

In the various embodiments, the intelligent icons can be configured to concisely describe an individual's medical conditions. For example, the shape and/or content of the intelligent icon can be selected to convey such information succinctly. Moreover, the intelligent icons can be configured to immediately link to specific medical records describing the medical condition in detail. In this manner, a physician or other provider can quickly access critical patient information, and be aware of potential hazards to treatment, such as allergies, blood thinners, or critical impairments.

In some embodiment of the invention, one intelligent icon can provide access to multiple other intelligent icons. That is, some medical conditions may be cause by a combination of medical issues. Accordingly, selection of the intelligent icon can cause the display to present additional intelligent icons associated with each of the underlying medical issues.

In some embodiments of the invention, embedding of related information within the intelligent icon is provided, without necessarily disturbing its appearance. These embodiments can also involve implementing methods to lock the embedded data, encrypt it, and/or reveal it on command. For example, the intelligent icons can incorporate password features so as to limit access to the data available via the intelligent icons. In some cases, the password and/or authentication program can be incorporated into the intelligent icon itself. In other cases, the password and/or authentication program can be incorporated into an external application or program, and the accessing of the intelligent icon can cause such external programs to be invoked.

The embedded related information may include one or more links to sources of information associated with medical condition, links to the patient's medical records in one or more healthcare information systems, data relating to the identity of the individual, an image of the individual, an identification of primary providers for the individual, baseline medical information, and/or any other information potentially critical for medical treatment. For example, the embedded related information can include information critical when providing traumatic care to the individual. In some embodiments, the intelligent icons can be configured so to provide a portal to the related information stored at one or more remote locations. In other embodiments, one or more portions of the related information may be actually embedded within the intelligent icon so as to allow the intelligent icon to contain at least a portion of a patient's core medical information that may be used without requiring connectivity to a larger network.

Such intelligent icons have a large number of uses beyond basic medical recordkeeping. For example, one potential utility is for the selecting of individuals and managing groups of such individuals in medical trails. That is, individuals, each represented by intelligent icons could be sorted by primary maladies, severity, and/or regional information, to name a few, that can be selectively unlocked, decrypted, parsed, and re-encrypted, while all the time being displayed and managed on a screen without comprising the identity of the individuals in the trial.

Another potential utility is utilizing such intelligent icons for displaying machine readable code (MRC) for the authentication of an individual for treatment. In operation, the code can be created when a patient is scheduled for treatment, verified for ascertaining an identity of the patient, and then transferred to a smart hand held device or paper to be presented on arrival for treatment. The MRC can be unique to the incidence of therapy or treatment, or span any number of therapies or treatments. It can be used by automated equipment to match the individual to treatments, infusions, medications, procedures and operations in order to reduce the incidence of medical errors.

In such embodiments, the intelligent icon may change in appearance and/or content (i.e., change the embedded information) as an individual progresses through a process. For example, if the intelligent icon is transferred to a smart handheld device, such as an intelligent handheld or personal identification device, the intelligent icon may initially display the Payer or Provider Logo or (Facial) ID Image when the patient checks in. Thereafter, as the patient progresses through a treatment process, the intelligent icon may change to indicate where in the treatment process the patient currently is in. Such changes can include changes in appearance or links to related information.

Further, various layers of information, such as images, text or executable code embedded within the intelligent icon may be routed to the display as required during the process. Further, as necessary for privacy or security (e.g., to be compliant to the Health Insurance Portability and Accountability Act or other security standard), a one-time authorization code, MRC, link into a database or records system, or other pertinent value, can be displayed for an identification and authorization procedure prior to a treatment step(s). This permits provisioning of a highly secure environment to allow providers immediate and direct access to patient records with little or no security or privacy concerns.

Once the MRC is processed and access to the patient records is granted, patient privacy is less of an issue since the provider is presumed to be accessing the patient records in a secure environment. However, but alerting a provider to medical conditions of the patient may still be necessary. Thus, the provider is alerted to medical condition(s), associated with the patient using one or more additional intelligent icons. In such cases, these intelligent icons can be selected so as to alert healthcare providers and professionals an overview of immediate concerns. For example, although a patient may be associated with a large set of medical records, each potentially associated with intelligent icon. However, rather than presenting all possible intelligent icons, the most pertinent intelligent icons can be presented. The pertinent icons can be selected, for example, on the type of provider, a current type of treatment or test, or the current type of facility, to name a few. In a more concrete example, diabetes and heart disease history may be important in an emergency situation. Accordingly, when a patient record is provided to emergency personnel or at an emergency facility, the record may be initially presented with only those intelligent icons associate with diabetes and heart disease to provide alerts to the emergency personnel. Alternatively, all potential intelligent icons can be presented, but those with particular importance can be highlighted. For example, pertinent intelligent icons can be highlighted by changes in appearance, size, motion, or any other change in presentation. In another example, an indicia or other marker can be added to the presentation of the intelligent icon to indicate an alert. In yet another example, the presentation of the intelligent icons can employ a sequential display starting with the more pertinent ones or a display in which movement is applied to the most pertinent ones to alert the provider.

In related embodiments, the intelligent icons can be stored in a patient's smart hand held device. When stored in a patient's smart hand held device, core information can be unlocked by responsible authority, decrypted with secure-controlled access keys, and sequentially displayed on the screen of the hand held device for printing or presentation for authentication and/or subsequent treatment processes. Core Information could include the above-mentioned MRC, the patient's image, biometric information, fingerprints, and a basic record of medical history. Additionally, for certain treatments, access can be provided to additional pertinent information for the treatment process.

In some embodiments, the patient's handheld device could stamp the time and GPS location whenever presented. In some cases, such time and location information could be uploaded to a database of a healthcare system over a secure communications link for enhanced patient tracking. Similarly the same information can be transferred by the provider, over a secure communications and matched in the healthcare system for provider payment authentication/authorization. In this manner, fraud can be prevented since it would be very difficult for the provider to obtain the patient's unique MRC for the given event and match the time and GPS position for purposes of verifying treatment by the provider occurred. That is, the present invention can prevent fraudulent claims by providers by requiring that a patient's one-time preauthorization code, identification with potential biometrics (facial image, voice id, or the like), and a treatment time and position must match a central database.

Although the present invention has been discussed primarily with respect to managing healthcare resources and patients, the present invention can also be used for managing other types of limited resources and users. For example, the present invention is also applicable for managing the tracking, loaning, "gifting," and/or "re-gifting" of software or digital content. In another example, the present invention can be utilized for managing the allocation of medical equipment and supplies, military equipment and supplies, or any other types of equipment and/or supplies. In still another example, the present invention can be utilized for providing secure identification of individuals to improve security processes at borders, during elections, or for buildings, to name a few. In such cases, an MRC and an intelligent icon can be embedded in passports and visas for the purposes of assisting border security.

FIG. 1 shows an example of how intelligent icons can be attached to a patient record in an advanced healthcare information system. First, a cardiologist can attach or select an icon (1) for the patient record that indicates that a chronic coronary artery disease condition is diagnosed. The cardiologist can expressly attach the icon in some cases by selecting from a bank of icons associated with different cardiovascular conditions. In other cases, the icon may be automatically selected when the cardiologist inputs the disease condition or selects the disease condition from a list or the like. As noted above, patient information can be embedded within the icon. The icon is then forwarded, via a physician-provider portal (2) and a software bus (3) to a database (6). The software bus can be, for example, an network between the multiple providers and the database.

Similarly, a dentist can attach or select another icon (4) for the patient record that indicates some periodontal condition being diagnosed. As described above, the dentist can expressly attach the icon in some cases by selecting from a bank of icons associated with different dental conditions. In other cases, the icon may be automatically selected when the dentist inputs the disease condition or selects the disease condition from a list or the like. As noted above, patient information can be embedded within the icon. The icon is then forwarded, via a physician-provider portal (5) and the software bus (3) to the database (6).

The records in the database are used to support a patient centric healthcare records system. Thus, in the example of FIG. 1, retrieving a patient record (7) provides a patient record including at least two intelligent icons, namely the intelligent icons for coronary artery disease (1) and the periodontal condition (4).

The result of this arrangement is that the dual intelligent icons in the patient record (7), alert providers of potential issues. For example, when the patient record (7) is presented to the cardiologist (8), it alerts the cardiologist to coordinate with the dentist for treatment. For example, to eliminate any dental infection and/or plaque that might have an adverse effect on cardiovascular health. In a similar fashion, when the patient record is presented to the dentist (9), dentist is put on alert to be mindful of actions that can affect those with cardiovascular disease. For example, to avoid depressing a potentially fragile heart with excessive anesthesia. Thus, cooperative treatment is possible with requiring direct interaction between providers or review of records from multiple providers.

In the various embodiments, the intelligent icons generally follow standards of the operating systems that support them, in order to allow interoperability and portability of applications. Of particular interest is that fact that each icon in a modem operating system is formed using thousands of pixels or picture elements (pels), each capable of presenting one color from a palette of thousands of colors. For example, if one were to right-click on the Internet Explorer icon in Windows 7, you may see that an icon typically contains approximately 4K bytes of information. This may be a 32×32 image array defining 1024 pels in the image array. Each pel can have a color depth of 4 bytes (or 65536 colors) for each pel. Or, it may be a 48×48 array with a color depth of 2 bytes per pel. The size and color depth are adjustable by both the operating system and the application—but this is typical. Some icons are hundreds of thousands of bytes, as the standard allows up to 256×256 bit images with color depth of 4 bytes and then there can be multiple images with animation. Further, even if one looks at the simple case of just showing a monochrome icon with a color depth of 2 bytes, this will define 65,536 levels of grey at each pel position in the image.

The number of colors associated with the thousands of pels in icons can therefore be used in the various embodiments to embed information via adjustment of the pels, without appreciably affecting the presentation of an icon. For example, although the eye will discern at least 100,000 colors, most individuals are incapable of perceiving the difference between any 2 nearly identical colors. That is, very few people are able to perceive any contrast between color #65535 and color #65536.

Consider an image that has only a 5-bit depth (32-levels of intensity difference), and an embedded character inside that is one bit different than the background. Even a modem computer monitor driven by a high quality display adapter would have difficulty displaying the image in a manner in which the character would be visible. It can be said that such a difference is equivalent to the impact of the lesser 26 or 32 significant bits in the monochrome image.

Consider a more modem image type in which is 2 bytes (16-bits) deep, the contrast difference would be about 2 thousand times less. Color helps the eye discern differences, yet the single bit difference was in a 32-bit (4 billion colors) image, contrast would be 135 million times less. The net result of this is that information encoded into the lesser 2-bytes of information is essentially invisible behind a colorful image in the more significant 2-bytes of color depth. Further, logical operations could completely mask anything in the lesser 2-bytes of color depth too. Thus, a private space is available to embed or hide information.

Figure 2:
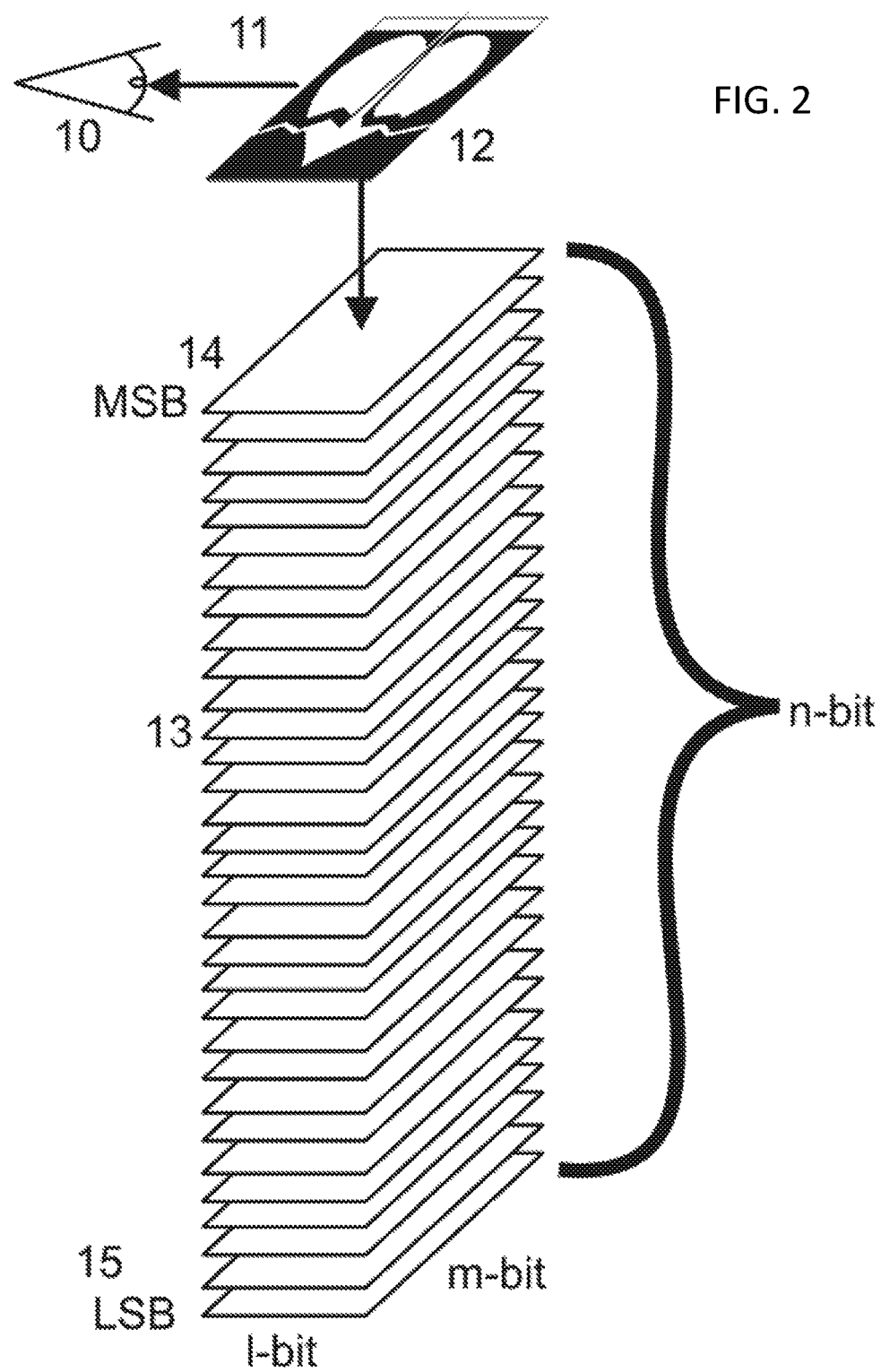
FIG. 2 is a description of a multilayer format for intelligent icons in accordance with the various embodiments.

FIG. 2 is a schematic example of the organization of an intelligent icon in accordance with the various embodiments. The eye (10) receives (11) the combined image (12) that is the result of what can be considered n planes of image (13). The top plane (14) that is associated with the most significant bit (MSB) of color depth can impact the intensity 50%. A purely black and white icon as in (12) would only need this plane. The next lower plane would change intensity only 25%. If there are n=32 planes, the plane (15) associated with the least significant bit would only have an impact of 0.000000002% (1/4.3 billion). Anything hidden on this last plane is essentially invisible—and again logical operations in the display controller or presentation software can completely mask information stored in the lesser significant bits of the intelligent icon.

Figure 3:
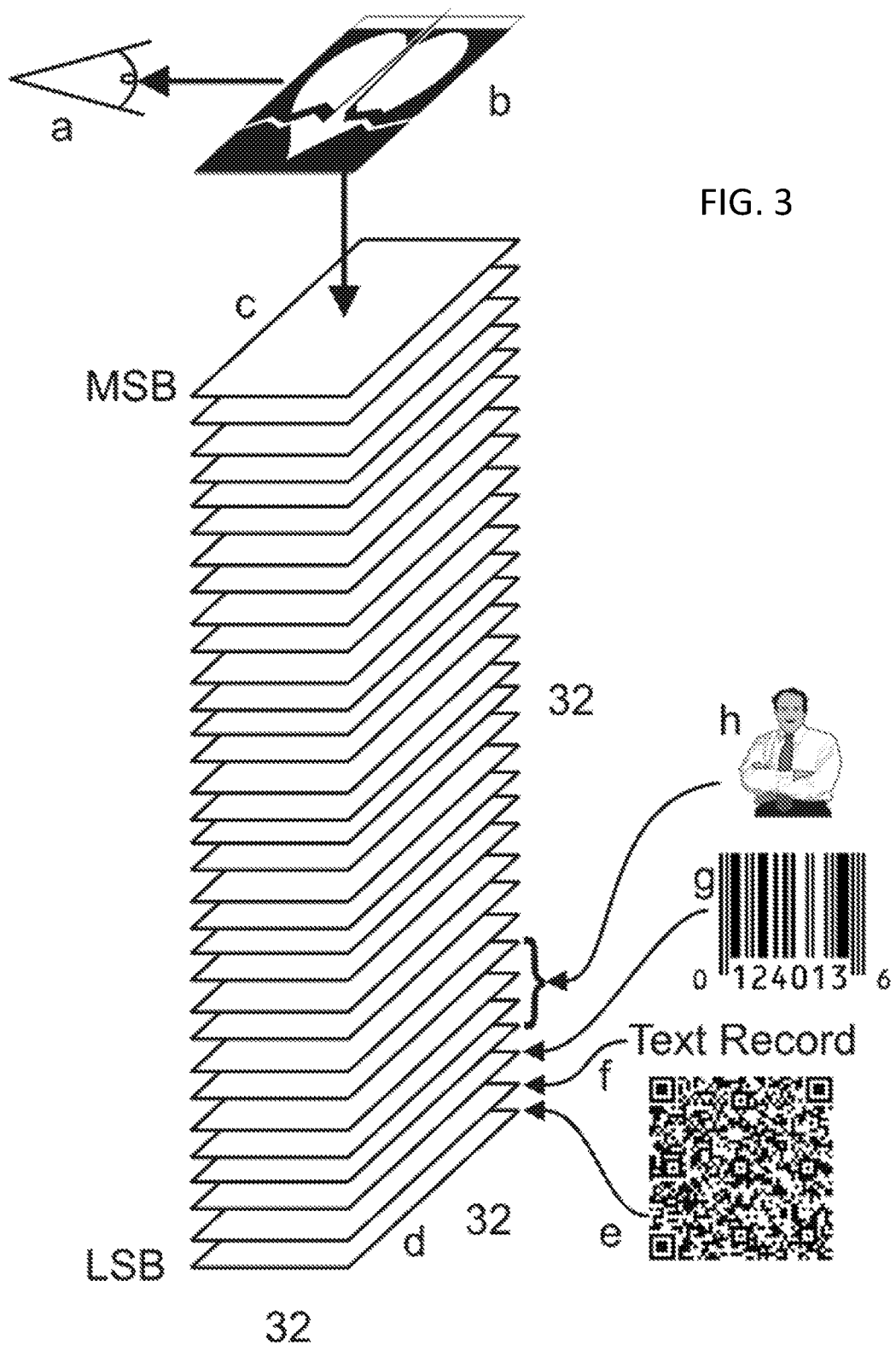
FIG. 3 is a description of embedding of information in an intelligent icon in accordance with the various embodiments.

FIG. 3 shows a second schematic example showing how machine readable images, text and images can be stored in the lesser significant bit-planes of an intelligent icon in accordance with the various embodiments. As in FIG. 2, the eye (a) sees an icon image (b), that might be as little as 4 bits deep. Windows 3 icons were typically 4 bits deep. While their primary looking colors were somewhat primitive looking by modem standards, they were acceptable, and an 8-bit deep icon looks almost as good as a 16-bit or 32-bit icon. An 8-bit color depth leaves 24 bit planes to embed information within the intelligent icon. Such information can include, for example, standard machine readable codes (e) and (g) or proprietary MRCS and text records. A usable image (h) can be created in 4 planes, by color separating the image, or using simple 4-bit encoding.

Figure 4:
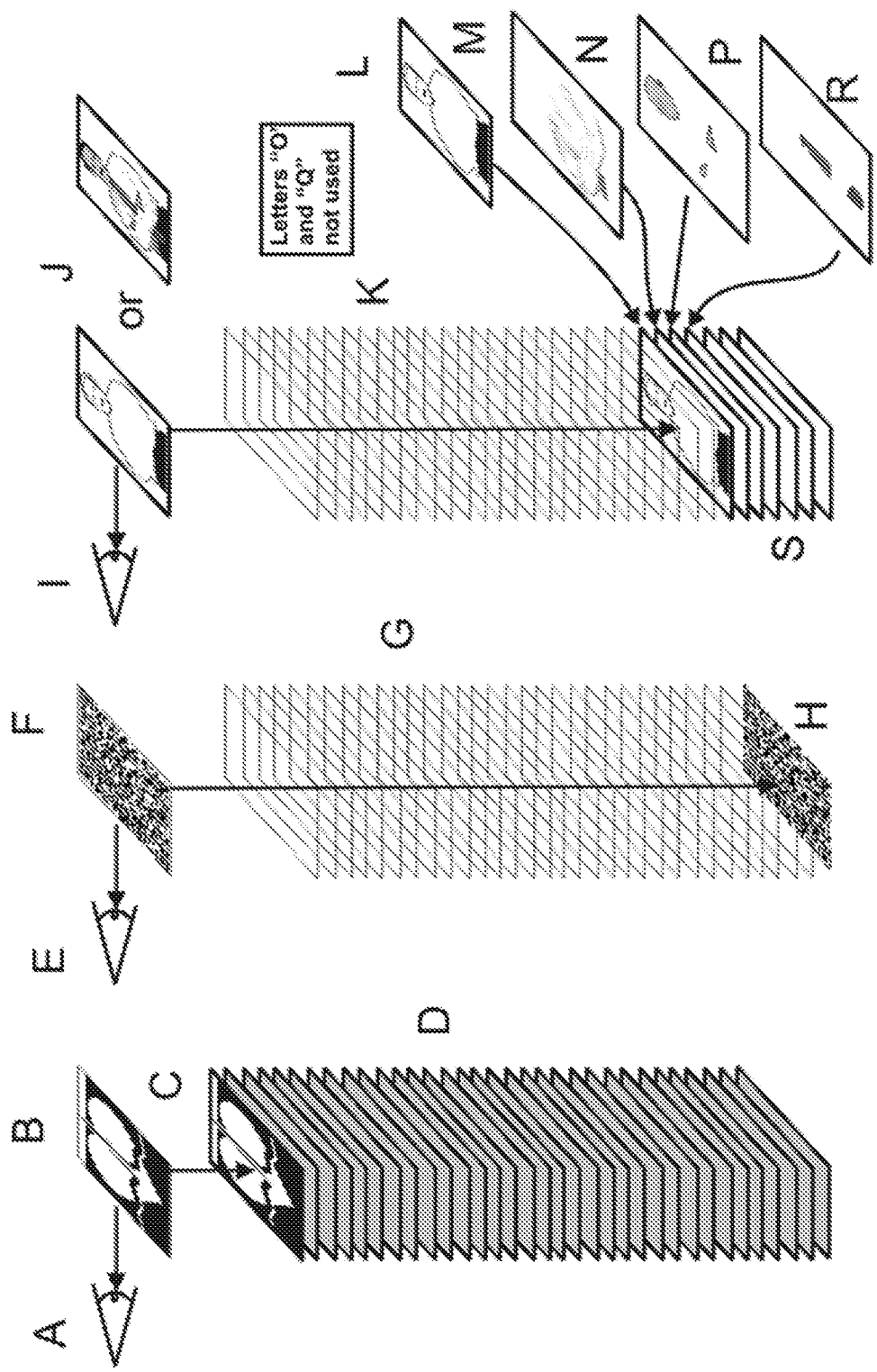
FIG. 4 is an illustration depicting the incremental presentation of intelligent icon data in accordance with the various embodiments.

FIG. 4 shows one of several means where the embedded information can be incrementally presented in accordance with the various embodiments. In stack (D), the eye (A) sees the top plane, or planes, (C) which hold the intelligent icon image (B). In stack G, when single plane information is stored on a lesser significant plane (H), it is made visible as (F) when the display controller or software makes the planes above transparent (all zero), or the plane (H) is moved to the top MSB position. A multi-plane image (L) comprised of planes (M,N,P,R) is exposed plane by plane by making the planes (K) above it transparent, thereby potentially revealing single plane (S) information underneath.

Figure 5:
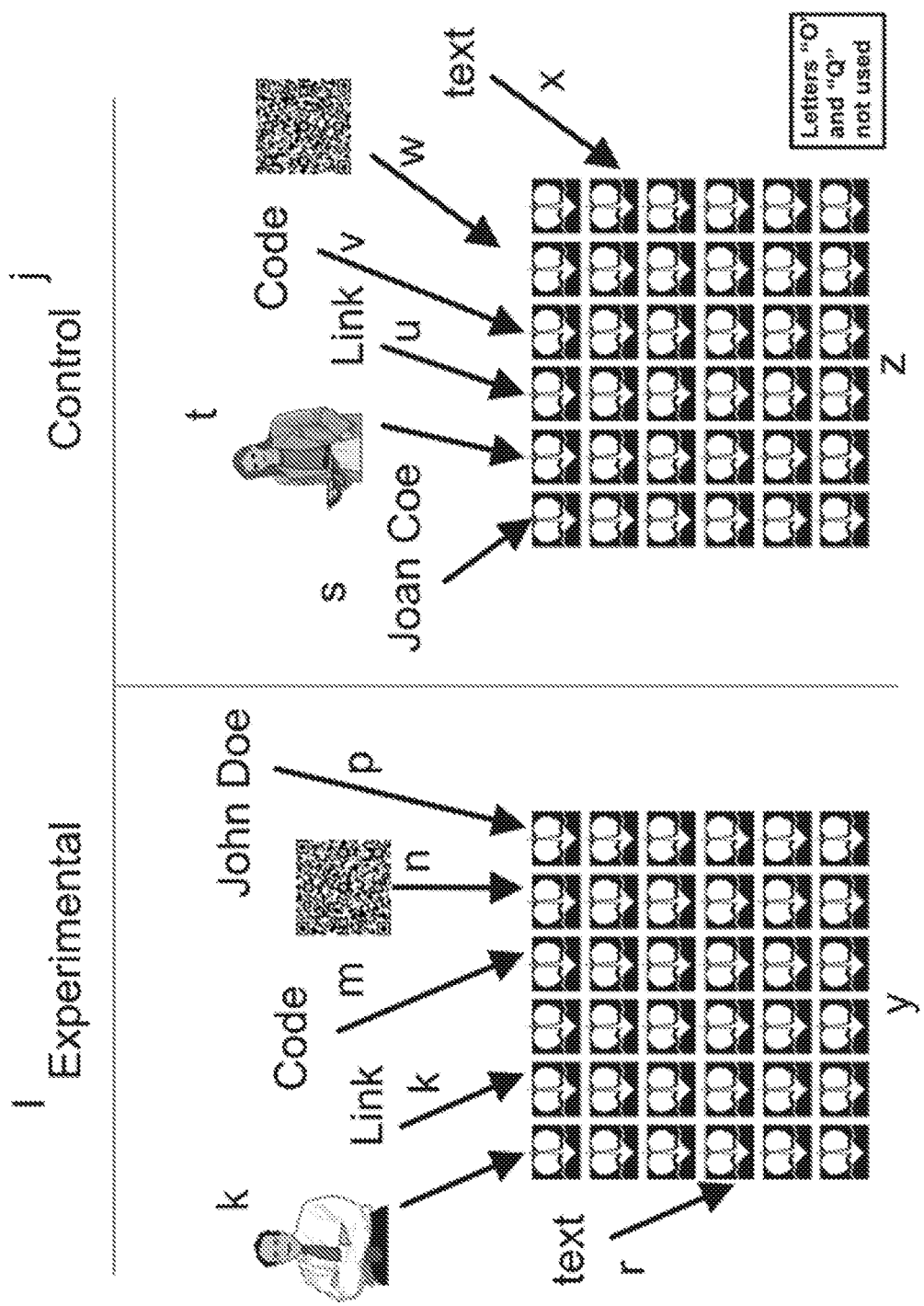
FIG. 5 is a chart that illustrates Visually De-identified double blind trials using intelligent icons in accordance with the various embodiments.

FIG. 5 shows how the visible icon can show individuals with a common malady, in this case designated by the heart icon, with the information below the intelligent icon locked, or encrypted. The intelligent icons are organized and managed on screens into experimental (i) and control (j) groups (y and z respectively). However, they may be designated by MRCs (n) or (w), or text codes (m) or (v) that is not human readable or identifiable. At the end of the test, the locked or encrypted identifying information (text r, image k, link k, name p) or (names, image t, link u, text x) can be unlocked, decrypted and revealed.

In some embodiments, layers of information, e.g. slices or layers within an MRI, can be assembled from associated layers of information on the planes of the intelligent icon in a manner similar as the formation of the facial image is created in layers, as in FIG. 4. Further, the intelligent icon may similarly show a history or progression of a malady. For example, individual stages of progression a melanoma may be defined in a few layers of the intelligent icon, with multiple images depicting the progression of the disease. The intent is that the intelligent icon goes beyond being a "Medic Alert" and can be configured to provide a synopsis of a patient's disease and treatment history. It may be rapidly transmitted over slow media and may be the only record available in some instances.

Figure 6:
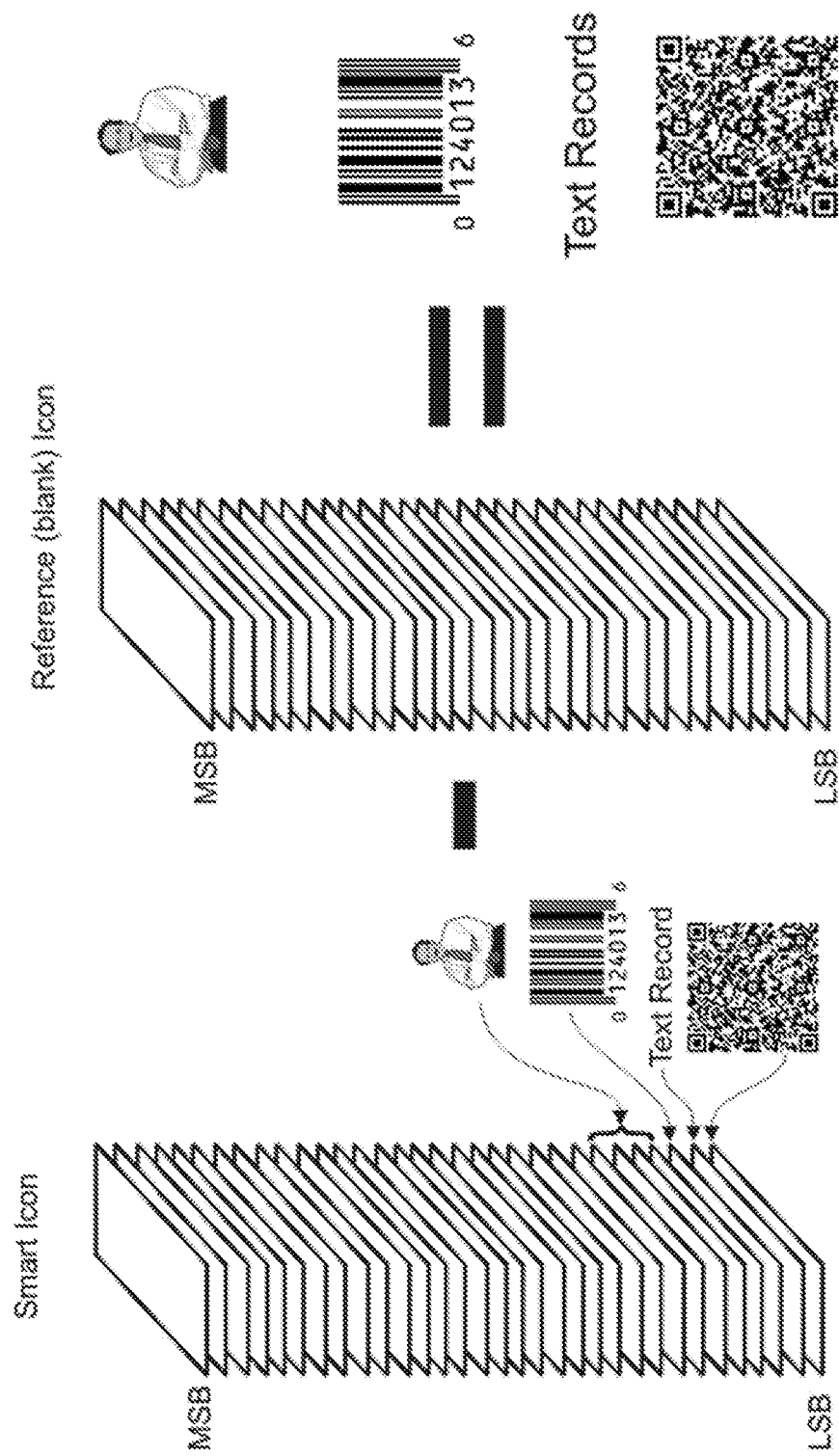
FIG. 6 is an illustration of subtraction of a reference icon from intelligent icons in accordance with the various embodiments to reveal hidden data.

FIG. 6 shows how simple subtraction of a reference icon with lesser significant planes blank can reveal the hidden information in an intelligent icon in accordance with the various embodiments. If the image for the intelligent icon is defined solely by the most significant 8-bits then (3×32× 32=3096) bytes can be stored within the remainder of the intelligent icon. This is about 3 pages of double spaced text, 6 sectors on the hard disk, or perhaps a small compressed x-ray, MRI, ultrasound or other image.

Figure 7:
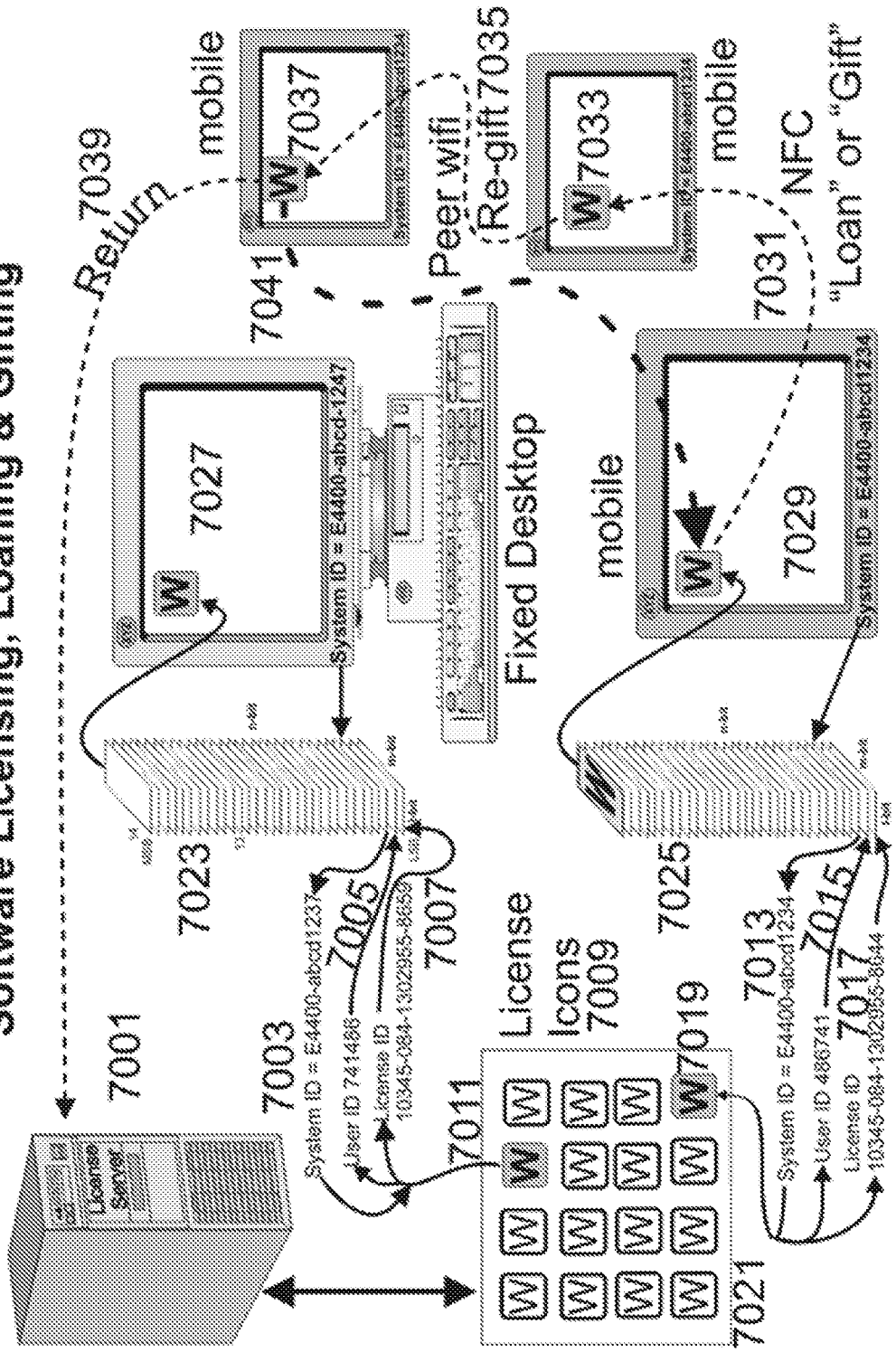
FIG. 7 is an illustration of Software Leasing, Loaning, and gifting in accordance with the various embodiments.

As noted above, the various embodiments have utility beyond medical records. This is illustrated in FIG. 7, which shows an alternative embodiment for software leasing. In a typical existing scenario a number of software licenses for a larger number of users are juggled and assigned as required. Given that many desktops sit idle, or rarely use applications, this mechanism can save an enterprise money by getting maximum utilization from the purchased software that executes on the client systems.

Further, some applications execute applications in the server and provide a "virtual desktop" on the client system. This configuration typically requires CALs or Client Access Licenses on every client as compensation for the interface that is presented or repeated from the server's OS. Clients are connected typically by fast networks as, depending on the specific product, the CAL, application or parts of the application are remotely transferred to, or activated in the client systems. This architecture is obviously less effective where connectivity is slow, intermittent or absent, as in many mobile systems.

Intelligent Icons would internalize the license for the client application. That is, the intelligent icon itself then becomes the means to access software that is stored dormant, or (if small enough) loaded in part or in whole as required on remote machines. It would appear on a desktop when the application is enabled. License validation could occur in the license server or by polling systems by interaction with active intelligent icons—those associated with valid licenses. Further, an intelligent icon could be transferred between systems in a sequentially re-usable resource fashion when the license server was unavailable—or temporarily between mobile systems without connectivity. The transfer can be temporary, in order to prevent usable duplication of the enabling feature of the intelligent icon. Eventually the systems would need to connect to the licensing server for a renewal of the lease or a timeout would occur. If polled, any system could yield its license ID, USER ID and System ID for a matchup verification.

With a size of 4K-bytes, or 32 k-bits, an intelligent icon can be transferred to the client in less than a millisecond with 50 ms software overheads dominating the actual transfer speed on most wired and wireless networks (100 m-bit or faster). 4G LTE cellular systems offer 5-12 M-bit service and the latency would be about the same due to software overheads that would dominate in such small transfers. Net, with connectivity, an intelligent icon could function almost transparently and without connectivity, it could still be loaned, or gifted to another system, which could in turn re-gift the intelligent icon to another system. The transfers would be legitimate, so long as the system and user IDs were consistent with a text file also stored in the intelligent icon. This information could be compressed to 32 bytes per system, enabling approximately 100 'friends and family" who could be authenticated to temporarily be loaned or gifted the intelligent icon. In some embodiments, the loaned, gifted or re-gifted icon can be returned to its assigned system periodically, to permit a restart of the timeout. Consequently, due to the low overhead to logically "move" an icon, mobile systems can operate much as localized clients within the Enterprise's physical boundaries when connectivity was available. Further, itinerant mobile systems could be without connectivity for some period of time and still be active. The result is that a common architecture could be used for all systems, local desktops, mobile systems and intermittently connected mobile systems.

Another related embodiment is where mobile systems operate without a license server and juggle the intelligent icons by transfers within the authorized group by an inter communication means, such as bit torrent. Icons would be offered to the torrent swarm, constituted by authorized members of the 'friends and family" file defined earlier when no longer required by one mobile system and destroyed by the managing software in each system. Any system in the swarm could also monitor the transfer of smart intelligent icons with licenses and accumulate an audit for validation purposes. Indeed, there is no reason why this form of server-less software leasing could not work if all systems in an enterprise were mobile capable.

Referring back to FIG. 7 as an example of how such a system might work, the licensing server (7001) contains 16 licenses, for 96 potential users in the "friends and family list" defined above. The active license intelligent icons (7011, 7019) would be displayed on the server's screen (7009) along with unassigned in-active intelligent icons. Rolling over the active intelligent icons would yield the leased license information of System ID (7003) for desktop system (7027 or 7013) or for mobile system (7029) with associated users (7005 and 7015, respectively) and assigned licenses (7007 and 7017, respectively). This information is stored in the lesser 3 significant bit planes of the intelligent icons (7023) for the desktop system (7027) and the intelligent icon (7025) for the mobile system (7029). This information would be essentially invisible, encrypted, or could be suppressed by actions of the display controller hardware on the intelligent icons (7023 and 7025) if required.

Mobile system (7029) travels to Timbuktu to visit with the Dalai Llama, and write the Great American Service Plan. Connectivity is not available, yet with 2 coworkers, using similar systems (7033 and 7037), can still work on alternate 8 hour shifts. The three travelers are included in the "friends and family list" as defined earlier and each may use the license for a period of 24 hours before it must be returned to the license server (7001) or to the original assigned user (7029).

At the end of the first shift, a first mobile system (7029) "gifts" or transfers the intelligent icon (7031) and license to a second mobile system (7033) by a near field communication (NFC) or other communications link and the (7025) icon disappears from the screen of the first mobile system (7029) and appears on the screen of the second mobile system (7033). A 24 hour timeout starts, where the license icon must be returned to first mobile system (7029) or the license server (70010, or it will be destroyed automatically.

The coworker continues on the creation of the GASP document for another 8 hours, whereupon, the license is "re-gifted" (7035) by transfer over to a third mobile system (7037). At this point, the license will expire in 24 hours unless returned: the user of mobile system (7037) may either return (7041) the license icon to first mobile system (7029) or wait until connectivity is available to transfer (7039) the license back to the server (7001). The three workers continue working on the GASP indefinitely by passing the license icon around within the timeout period.

It is conceivable that additional workers may be sent to help complete the document and as many users in a friends and family list may exchange intelligent icons. Indeed, reinforcements may come from different groups with different friends and family lists and theoretically any number of leased-license systems may be supported without connection to the licensing server (7001).

In time, if a branch office is established and additional new-hires bring new software that allows the exchange of smart intelligent icons via a bit torrent swarm without any need for connection to any licensing server. When the software vendor eventually arrives to audit the premises, simply rolling over the active intelligent icons on the systems reveals their "genuine" authenticity.

Still another alternative embodiment, as discussed above, is the implementation of a smart ID system, such as a smart passport and visa system. In the case of passports, an intelligent icon can be a license to travel that identifies the individual and young minor children as "friends and family". The list is encrypted, along with passport and visa data and the intelligent icon becomes installed on a smart phone, electronic passport, or other device carried by the traveler, after activation in the US or US embassy. At each port of entry, a MRC is displayed on the smart phone and an encrypted file is transferred by NFC back to the "licensing" server in the USA for validation. Additionally the intelligent icon can contains an image of the individual, biometric information, and/or even medical history and can link to healthcare systems in the cloud should background or medical information be required. In essence, the process is similar to smart intelligent icons in software leasing but obviously without the loaning, gifting or re-gifting capabilities.

Similarly, these intelligent icons could be used to manage troops on a battlefield, similar to the double blind test model and software leasing schemes. For example, the intelligent icon stored in a wearable computer can be configured to enable nearby weapons. The intelligent icon associates to MRCS and prevents firing on soldiers and equipment displaying a MRC embedded on uniforms and painted on equipment. The MRC can be scanned by laser prior to any targeting. Effectively the MRC is a flag. The objective is friend or foe identification and prevention of friendly fire.

Still another alternative embodiment, as discussed above, is the implementation of a hardware or equipment management system. For example an MRI machine might have a intelligent icon for the technician who fills it with coolant, another for the technician who operates it, and still one more intelligent icon for the professional who views and interprets the imaging. Indeed, the repair technician might have a unique intelligent icon that gives him diagnostic controls. In some cases, such intelligent icons can be provided in a nested arrangement, as discussed below.

Similarly, the intelligent icons as associated MRC controls previously defined have application in the deployment and authorization for use of medical equipment. Equipment displaying the appropriate MRC can be scanned by smart handheld devices, with an authenticating intelligent icon, and allocated for shared use medical centers and under triage scenarios.

Still another alternative embodiment is the implementation of nested intelligent icons. That is, the storage space within the intelligent icon can be used to define a structure of intelligent icons and their screens. For example, an intelligent icon can store a link (e.g., C:\Utilities\Nero\Burning\ROMPortable\Burning ROMPortable.exe). This link can be found in the properties of the window displayed by a right click of the intelligent icon. And typically one must start the program, with consequent delay, to see the many optional functions within. An alternate approach would be to include all of the links to these many optional functions within the intelligent icon. This is illustrated in FIG. 8.

Figure 8:
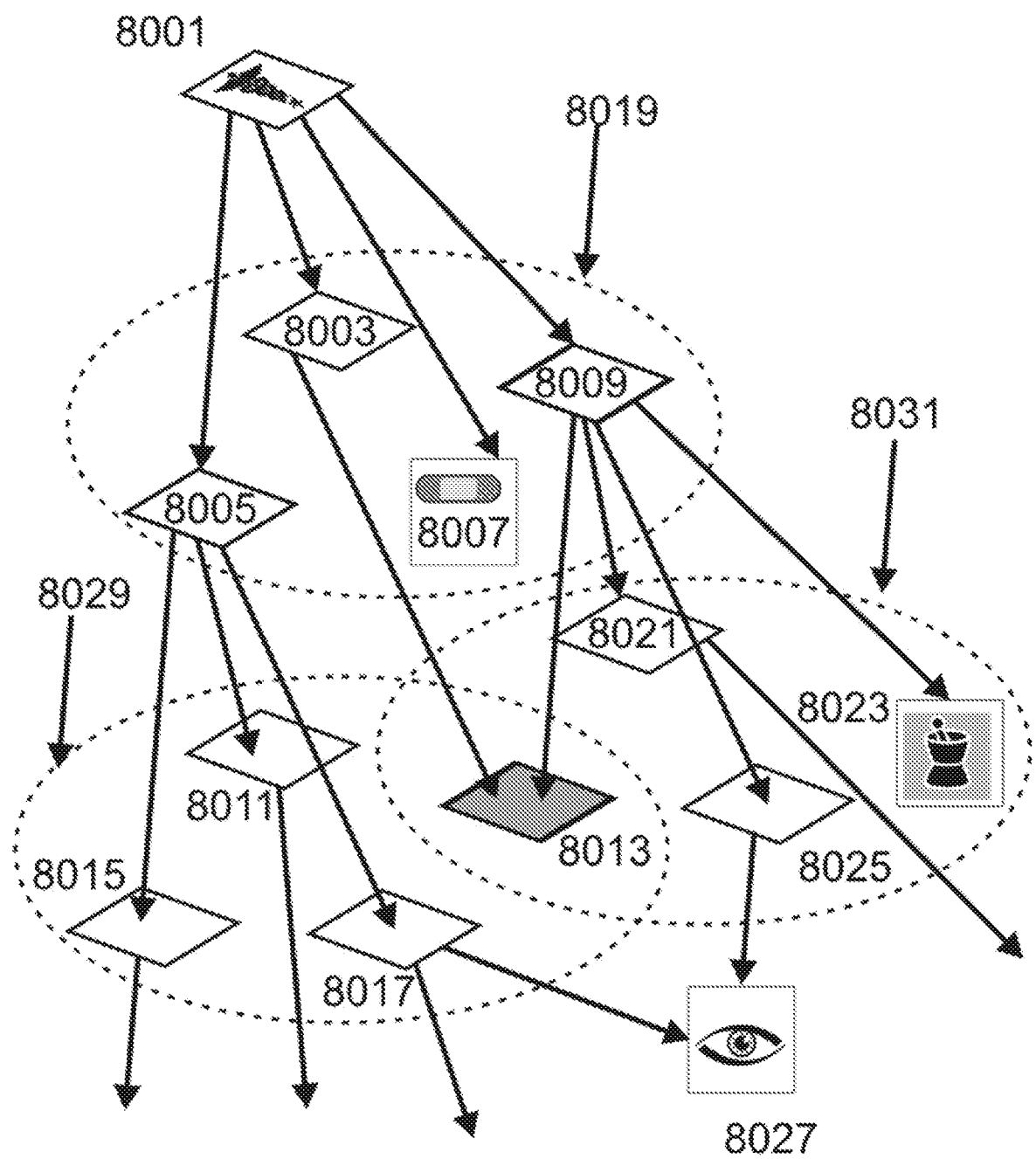
FIG. 8 Depicts the concept of nesting intelligent icons in accordance with the various embodiments

Referring to FIG. 8 a parent icon (8001) has daughter intelligent icons (8003, 8005, 8007, and 8009). Only one of these intelligent icons (8007) is an executable program, for which the band-aid icon is used. The others are in turn parent links to other intelligent icons, which in a hierarchical structure lead to other intelligent icons and in some cases executable programs (8023, mortar and pestle, or 8027, eye). For example icon (8005) leads to multiple intelligent icons (8011, 8013, 8015 and 8017). It should be noted that in some cases, different nested icons may be associated with different providers. Thus, such intelligent icons can have different permissions and functions. Further, to alert the user of regarding pertinent information, in a daughter icon, the part icon can be highlighted as discussed above. In some cases, the highlighting can be different for alerts related to the parent icon versus the daughter icon.

Some intelligent icons (8017, 8025, and 8009) lead to executable icons (8027, 8023). The remaining intelligent icons appear on the screens (8019, 8029, and 8031) which appear if an icon on that screen is selected.

In operation, the user selects an intelligent icon and if that intelligent icon is not an executable program, then very quickly the appropriate screen is painted. Painting the screen is at least an order of magnitude faster than initiating an executable program. This allows the selection and navigation to be significantly faster than the typical scenario and the number of intelligent icons per screen can be held only to the minimum required for the associated functions. By example, there are a number of separate functions within a presentation program. They are used to create the presentation, present the presentation, or print the presentation. This concept would nest all the optional sub functions, each with an independent icon, under a parent icon, such that navigation to a specific sub function would be much more rapid.

Further, only those functions required by a given user need be contained within an icon. A salesman for example might never create the presentation or edit it. Indeed, the salesman's management may only want those limited options to print or present. He would only need those intelligent icons leading to presentation and printing within an icon that he would use.

The icon could be customized for the salesman, where another might have the full set of functions. Indeed, when a user starts a system, they could have a customized hierarchical structure, unique to them and stored within their unique icon. If that icon were transferred to another system, it would carry that user's personalization.

Figure 9:
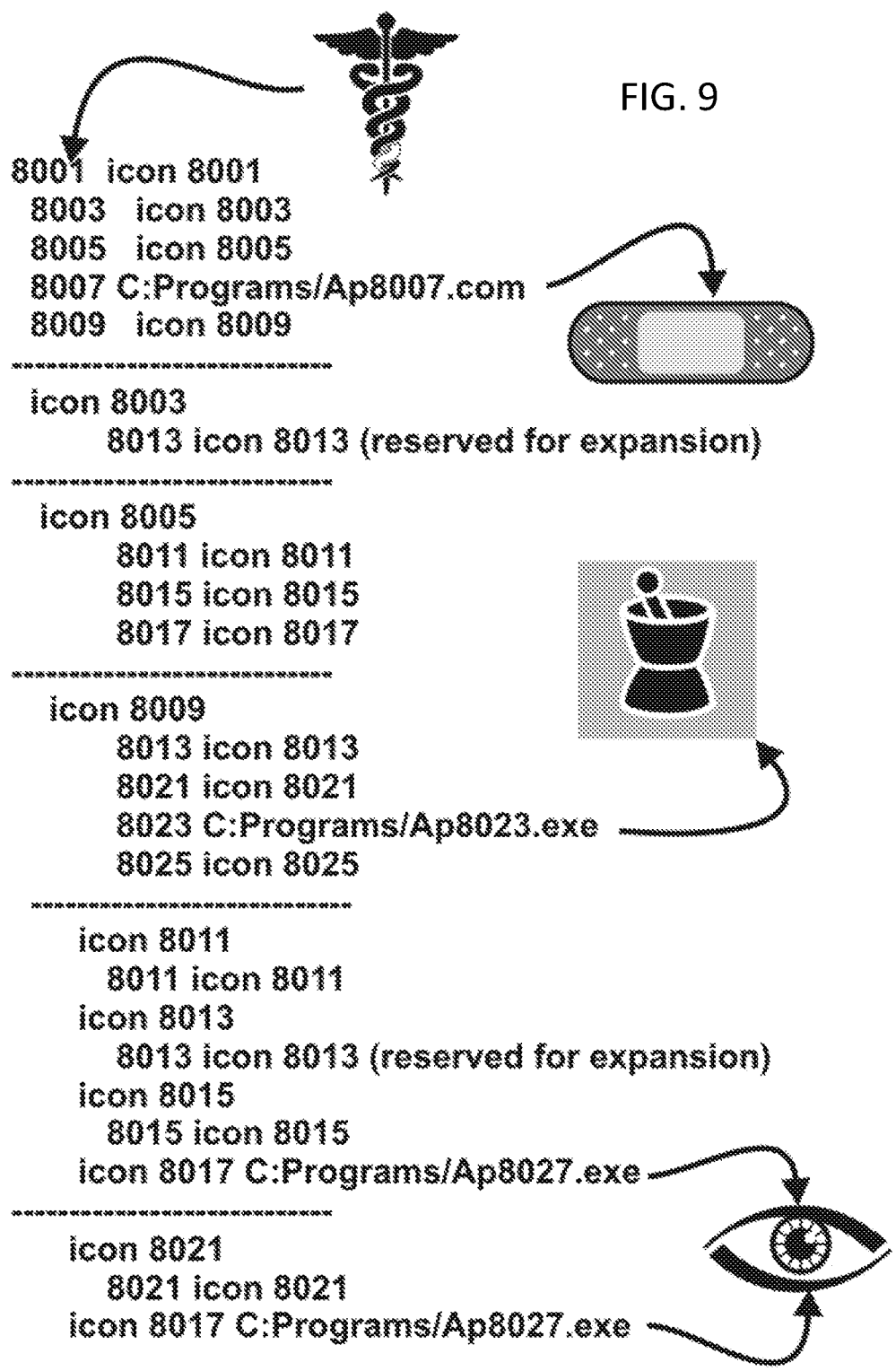
FIG. 9 is a list of subordinate referrals from each intelligent icon in FIG. 9.

Referring to now to FIG. 9, there is shown a list, depicting all the links under a given icon, for the structure of FIG. 8. This would be representative of the information stored in an icon for a given user, purpose, or system. Editing this list, would alter the custom configuration for a given specific user, purpose, or system.

In the list of FIG. 9, one can see that the hierarchy is infinitely expandable, that intelligent icons can lead uniquely to other intelligent icons, or that more than one icon can lead to an executable function, or to other intelligent icons that eventually do so. Because, navigation is much faster and that customization is more easily configured this structure is desirable for those advantages. Further, room for expansion for later augmentation of the structure can be reserved. It should be noted that the storage space required to contain information about a hierarchy of intelligent icons, such as those in FIG. 8 can be quite small. For example, the storage space can be less than 1 kilobyte. Given the potential storage space available in an intelligent icon, extremely complex structures and hierarchy are entirely feasible.

Figure 10A:
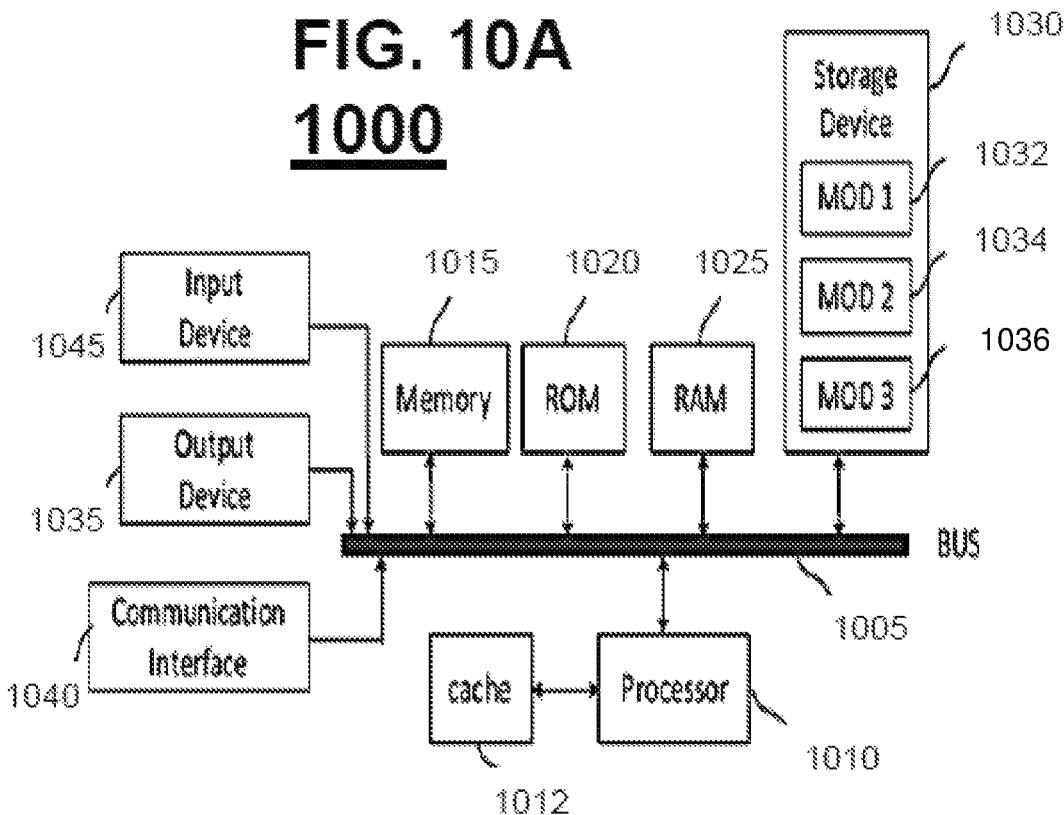
FIG. 10A and FIG. 10B illustrate exemplary possible system configurations for carrying out any aspects of the present invention.
Figure 10B:
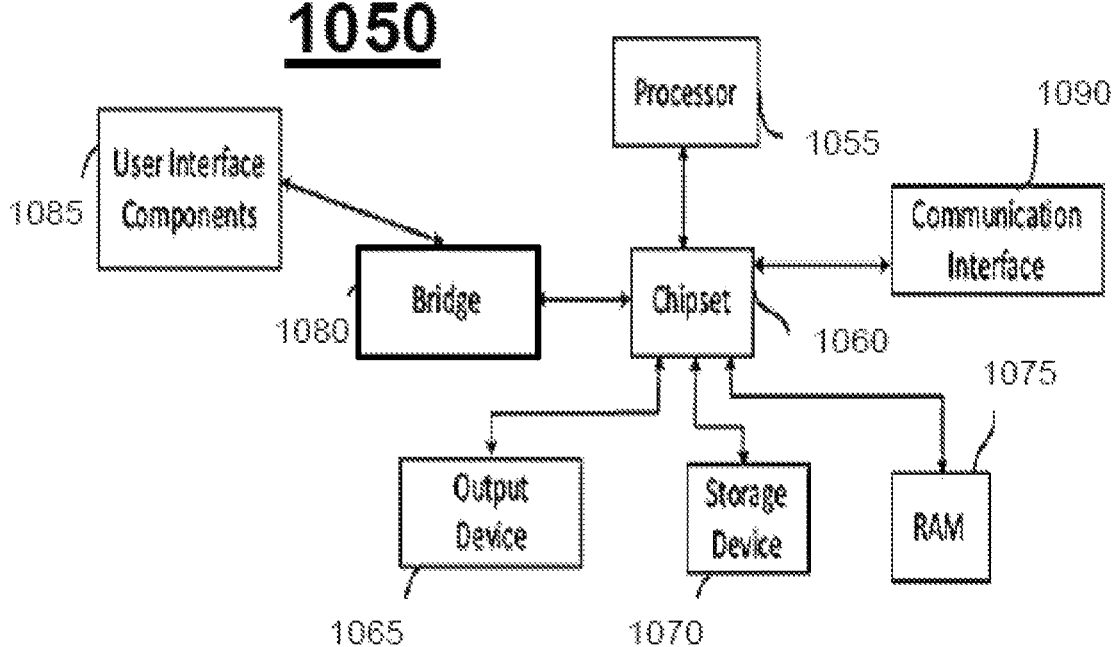

FIG. 10A and FIG. 10B illustrate exemplary possible system configurations. The more appropriate configuration will be apparent to those of ordinary skill in the art when practicing the present technology. Persons of ordinary skill in the art will also readily appreciate that other system configurations are possible.

FIG. 10A illustrates a conventional system bus computing system architecture 1000 wherein the components of the system are in electrical communication with each other using a bus 1005. Exemplary system 1000 includes a processing unit (CPU or processor) 1010 and a system bus 1005 that couples various system components including the system memory 1015, such as read only memory (ROM) 1020 and random access memory (RAM) 1025, to the processor 1010. The system 1000 can include a cache of high-speed memory connected directly with, in close proximity to, or integrated as part of the processor 1010. The system 1000 can copy data from the memory 1015 and/or the storage device 1030 to the cache 1012 for quick access by the processor 1010. In this way, the cache can provide a performance boost that avoids processor 1010 delays while waiting for data. These and other modules can control or be configured to control the processor 1010 to perform various actions. Other system memory 1015 may be available for use as well. The memory 1015 can include multiple different types of memory with different performance characteristics. The processor 1010 can include any general purpose processor and a hardware module or software module, such as module 1 1032, module 2 1034, and module 3 1036 stored in storage device 1030, configured to control the processor 1010 as well as a special-purpose processor where software instructions are incorporated into the actual processor design. The processor 1010 may essentially be a completely self-contained computing system, containing multiple cores or processors, a bus, memory controller, cache, etc. A multi-core processor may be symmetric or asymmetric.

To enable user interaction with the computing device 1000, an input device 1045 can represent any number of input mechanisms, such as a microphone for speech, a touch-sensitive screen for gesture or graphical input, keyboard, mouse, motion input, speech and so forth. An output device 1035 can also be one or more of a number of output mechanisms known to those of skill in the art. In some instances, multimodal systems can enable a user to provide multiple types of input to communicate with the computing device 1000. The communications interface 1040 can generally govern and manage the user input and system output. There is no restriction on operating on any particular hardware arrangement and therefore the basic features here may easily be substituted for improved hardware or firmware arrangements as they are developed.

Storage device 1030 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1025, read only memory (ROM) 1020, and hybrids thereof.

The storage device 1030 can include software modules 1032, 1034, 1036 for controlling the processor 1010. Other hardware or software modules are contemplated. The storage device 1030 can be connected to the system bus 1005. In one aspect, a hardware module that performs a particular function can include the software component stored in a computer-readable medium in connection with the necessary hardware components, such as the processor 1010, bus 1005, display 1035, and so forth, to carry out the function.

FIG. 10B illustrates a computer system 1050 having a chipset architecture that can be used in executing the described method and generating and displaying a graphical user interface (GUI). Computer system 1050 is an example of computer hardware, software, and firmware that can be used to implement the disclosed technology. System 1050 can include a processor 1055, representative of any number of physically and/or logically distinct resources capable of executing software, firmware, and hardware configured to perform identified computations. Processor 1055 can communicate with a chipset 1060 that can control input to and output from processor 1055. In this example, chipset 1060 outputs information to output 1065, such as a display, and can read and write information to storage device 1070, which can include magnetic media, and solid state media, for example. Chipset 1060 can also read data from and write data to RAM 1075. A bridge 1080 for interfacing with a variety of user interface components 1085 can be provided for interfacing with chipset 1060. Such user interface components 1085 can include a keyboard, a microphone, touch detection and processing circuitry, a pointing device, such as a mouse, and so on. In general, inputs to system 1050 can come from any of a variety of sources, machine generated and/or human generated.

Chipset 1060 can also interface with one or more communication interfaces 1090 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1055 analyzing data stored in storage 1070 or 1075. Further, the machine can receive inputs from a user via user interface components 1085 and execute appropriate functions, such as browsing functions by interpreting these inputs using processor 1055.

It can be appreciated that exemplary systems 1000 and 1050 can have more than one processor 1010 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some configurations the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Claim language reciting "at least one of" a set indicates that one member of the set or multiple members of the set satisfy the claim. Tangible computer-readable storage media, computer-readable storage devices, or computer-readable memory devices, expressly exclude media such as transitory waves, energy, carrier signals, electromagnetic waves, and signals per se.

While various aspects of the present technology have been described above, it should be understood that they have been presented by way of example only, and not limitation. Numerous changes to the disclosed aspects can be made in accordance with the disclosure herein without departing from the spirit or scope of the present technology. Thus, the breadth and scope of the present technology should not be limited by any of the above described aspects. Rather, the scope of the present technology should be defined in accordance with the following claims and their equivalents.

Although the present technology has been illustrated and described with respect to one or more implementations, equivalent alterations and modifications will occur to others skilled in the art upon the reading and understanding of this specification and the annexed drawings. In addition, while a particular feature of the present technology may have been disclosed with respect to only one of several implementations, such feature may be combined with one or more other features of the other implementations as may be desired and advantageous for any given or particular application.

The terminology used herein is for the purpose of describing particular aspects only and is not intended to be limiting of the present technology. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this present technology belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A system for displaying medical information via intelligent icons, comprising:
   one or more processors; and
   a computer-readable medium having stored thereon a plurality of instructions for causing at least one of the one or more processors to:
      receive health record data associated with an individual;
      generate a base image indicative of a medical condition associated with the individual; and
      encode at least a portion of the received health record data in a plurality of original pixels of the base image to produce an intelligent icon, the intelligent icon including a modified base image having a plurality of modified pixels, the plurality of modified pixels being configured to be displayed on a display device as a representation of the modified base image such that the representation of the modified base image displayed on the display device is distinguishable to a human eye as compared to the base image when displayed on the display device, and the visual difference between the modified base image and the base image being indicative of a treatment progress associated with the individual.

2. The system of claim 1, wherein the at least one of the one or more processors is further caused to:
receive a plurality of intelligent icons, each of the plurality of intelligent icons being associated with a different individual;
sort the plurality of intelligent icons by primary maladies, severity, regional information, or any combination thereof; and
display the sorted plurality of intelligent icons without compromising the identity of the different individual associated with each of the plurality of intelligent icons.

3. The system of claim 1, wherein the base image is selected from a pool of base images based on characteristics of the medical condition associated with the individual.

4. The system of claim 1, wherein the encoded portion of the health record data includes one or more links to (i) sources of information associated with one or more medical conditions of the individual, (ii) medical records associated with the individual in one or more healthcare information systems, (iii) data associated with an identity of the individual, (iv) an image of the individual, and (v) an identification of one or more primary providers for the individual.

5. The system of claim 1, wherein the portion of the received health record data is encoded into bits of different bit positions of the base image.

6. The system of claim 1, wherein the at least one of the one or more processors is further caused to:
receive a plurality of intelligent icons associated with the individual from one or more client devices;
extract the portion of the health record data from each of the plurality of intelligent icons;
aggregate the portion of the health record data from each of the plurality of intelligent icons to define a comprehensive medical record for the individual; and
transmit the comprehensive medical record to one of the client devices.

7. A computer-implemented method comprising:
receiving health record data associated with an individual;
generating a base image indicative of a medical condition associated with the individual; and
encoding at least a portion of the received health record data in a plurality of original pixels of the base image to produce an intelligent icon, the intelligent icon including a modified base image having a plurality of modified pixels, the plurality of modified pixels being configured to be displayed on a display device as a representation of the modified base image such that the representation of the modified base image displayed on the display device is distinguishable to a human eye as compared to the base image when displayed on the display device, and the visual difference between the modified base image and the base image being indicative of a treatment progress associated with the individual.

8. The computer-implemented method of claim 7, further comprising:
receiving a plurality of intelligent icons, each of the plurality of intelligent icons being associated with a different individual;
sorting the plurality of intelligent icons by primary maladies, severity, regional information, or any combination thereof; and
displaying the sorted plurality of intelligent icons without compromising the identity of the different individual associated with each of the plurality of intelligent icons.

9. The computer-implemented method of claim 7, wherein the base image is selected from a pool of base images based on characteristics of the medical condition associated with the individual.

10. The computer-implemented method of claim 7, wherein the encoded portion of the health record data includes one or more links to (i) sources of information associated with one or more medical conditions of the individual, (ii) medical records associated with the individual in one or more healthcare information systems, (iii) data associated with an identity of the individual, (iv) an image of the individual, and (v) an identification of one or more primary providers for the individual.

11. The computer-implemented method of claim 7, wherein the portion of the received health record data is encoded into bits of different bit positions of the base image.

12. The computer-implemented method of claim 7, further comprising:
receiving a plurality of intelligent icons associated with the individual from one or more client devices;
extracting the portion of the health record data from each of the plurality of intelligent icons;
aggregating the portion of the health record data from each of the plurality of intelligent icons to define a comprehensive medical record for the individual; and
transmitting the comprehensive medical record to one of the client devices.

13. A non-transitory computer readable medium having stored thereon a computer program for operating a server of an electronic records system, the computer program comprising a plurality of code sections for causing the server to:
receive health record data associated with an individual;
generate a base image indicative of a medical condition associated with the individual; and
encode at least a portion of the received health record data in a plurality of original pixels of the base image to produce an intelligent icon, the intelligent icon including a modified base image having a plurality of modified pixels, the plurality of modified pixels being configured to be displayed on a display device as a representation of the modified base image such that the representation of the modified base image displayed on the display device is distinguishable to a human eye as compared to the base image when displayed on the display device, and the visual difference between the modified base image and the base image being indicative of a treatment progress associated with the individual.

14. The non-transitory computer readable medium of claim 13, wherein the server is further caused to:
receive a plurality of intelligent icons, each of the plurality of intelligent icons being associated with a different individual;
sort the plurality of intelligent icons by primary maladies, severity, regional information, or any combination thereof; and
display the sorted plurality of intelligent icons without compromising the identity of the different individual associated with each of the plurality of intelligent icons.

15. The non-transitory computer readable medium of claim 13, wherein the base image is selected from a pool of base images based on characteristics of the medical condition associated with the individual.

16. The non-transitory computer readable medium of claim 13, wherein the encoded portion of the health record data includes one or more links to (i) sources of information associated with one or more medical conditions of the individual, (ii) medical records associated with the individual in one or more healthcare information systems, (iii) data associated with an identity of the individual, (iv) an image of the individual, and (v) an identification of one or more primary providers for the individual.

17. The non-transitory computer readable medium of claim 13, wherein the portion of the received health record data is encoded into bits of different bit positions of the base image.

18. The non-transitory computer readable medium of claim 13, wherein the server is further caused to:
- receive a plurality of intelligent icons associated with the individual from one or more client devices;
- extract the portion of the health record data from each of the plurality of intelligent icons;
- aggregate the portion of the health record data from each of the plurality of intelligent icons to define a comprehensive medical record for the individual; and
- transmit the comprehensive medical record to one of the client devices.

* * * * *